United States Patent
Wang et al.

(10) Patent No.: US 6,566,341 B1
(45) Date of Patent: May 20, 2003

(54) DERIVATIVE OF ISOINDIGO, INDIGO AND INDIRUBIN FOR THE TREATMENT OF CANCER

(75) Inventors: Longgui Wang, Flushing, NY (US); Xiaomei Liu, Flushing, NY (US); Ruihuan Chen, Foster City, CA (US)

(73) Assignee: Natrogen Therapeutics, Inc., Whitefish Bay, WI (US)

( * ) Notice: Subject to any disclaimer, the term of this patent is extended or adjusted under 35 U.S.C. 154(b) by 0 days.

(21) Appl. No.: 10/021,589

(22) Filed: Dec. 13, 2001

(51) Int. Cl.$^7$ ..................... C07D 295/02; A61K 31/403
(52) U.S. Cl. ........................................ 514/25; 536/4.1
(58) Field of Search .................... 564/372; 536/28.1, 536/4.1; 514/25

(56) References Cited

U.S. PATENT DOCUMENTS 5,696,092 A * 12/1997 Patierno et al. ................ 514/21

FOREIGN PATENT DOCUMENTS

| WO | WO 00/61555 | * | 5/1999 | .......... A61K/31/00 |
| WO | WO 99/62503 | * | 4/2000 | .......... A61K/31/404 |

OTHER PUBLICATIONS

Gray, Nathanael et al., Current Medicinal Chemistry, 199, vol. 6, 859–875.*

Merck Manual, 15$^{th}$ edition, 1987, pp. 1218–1219.*

Li, X.K., et al., *Huanglian, A chinese herbal extract, inhibits cell growth by suppressing the expression of cyclin B1 and inhibiting CDC2 kinase activity in human cancer cells*. Mol Pharmacol, 2000. 58(6): p. 1287–93.

DiPaola, R.S., et al., *Clinical and biologic activity of an estrogenic herbal combination (PC–SPES) in prostate cancer*. N Engl J Med, 1998. 339(12): p. 785–91.

Druker, B.J., et al., *Activity of a specific inhibitor of the BRC–ABL tyrosine kinase in the blast crisis of chronic myeloid leukemia and acute lymphoblastic leukemia with the Philadelphia chromosome*. N Engl J Engl J Med, 2001. 344(14): p. 1038–42.

Ji, X.J., et al., *Pharmacological studies of meisoindigo: absorption and mechanism of action*. Biomed Environ Sci, 1991. 4(3): p. 332–7.

Wang, L.G., et al., *Activation of casein kinase II in ML–1 human myeloblastic leukemia cells requires IGF–1 and transferrin*. J Leukoc Biol, 1995. 57(2): p. 332–4.

Gianni, L., et al., *Nonlinear pharmacokinetics and metabolism of paclitaxel and its pharmacokinetic/pharmacodynamic relationships in humans*. J Clin Oncol, 1995. 13(1): p. 180–90.

Wang, L.G., et al., *Down–regulation of prostate–specific antigen expression by finasteride through inhibition of complex formation between androgen receptor and steroid receptor–binding consensus in the promoter of the PSA gene in LNCaP cells*. Cancer Res, 1997. 57(4): p. 714–9.

Kong, M., et al., *Cyclin F regulates the nuclear localization of cyclin B1 through a cyclin–cyclin interaction*. Embo J, 2000. 19(6): p. 1378–88.

Kreis, W., D.R. Budman, and A. Calabro, *Unique synergism or antagonism of combinations of chemotherapeutic and hormonal agents in human prostate cancer cell lines*. Br J Urol, 1997. 79(2): p. 196–202.

Ohtsu, T., et al., *Clinical pharmacokinetics and pharmacodynamics of paclitaxel: a 3–hour infusion versus a 24–hour infusion*. Clin Cancer Res, 1995. 1(6): p. 599–606.

Morgan, D.O., *Principles of CDK regulation*. Nature, 1995. 374(6518): p. 131–4.

Buchdunger, E., A. Matter, and B.J. Druker, *Bcr–Abl inhibition as a modality of CML therapeutics*. Biochim Biophys Acta, 2001. 1551(1): p. M11–8.

Senderowicz, A.M., *Development of cyclin–dependent kinase modulators as novel therapeutic approaches for hematological malignancies*. Leukemia, 2001. 15(1): p. 1–9.

Wicki, A. and V. Niggli, *The Rho/Rho–kinase and the phosphatidylinositol 3–kinase pathways are essential for spontaneous locomotion of Walker 256 carcinosarcoma cells*. Int J Cancer, 2001. 91(6): p. 763–71.

Mitani, N., et al., *Inhibitory effect of berberine on the mediastinal lymph node metastasis produced by orthotopic implantation of Lewis lung carcinoma*. Cancer Lett, 2001. 165(1): p. 35–42.

Freitas, J.J., et al., *Walker–256 tumor growth causes oxidative stress in rat brain*. J Neurochem, 2001. 77(2): p. 655–63.

Damiens, E., et al., *Anti–mitotic properties of indirubin–3"–monoxime, a CDK/GSK–3 inhibitor: induction of endoreplication following prophase arrest*. Oncogene, 2001. 20(29): p. 3786–97.

Leclerc et al. "Indirubins Inhibit Glycogen Synthase Kinase–3β and DCK5/P25, Two Protein Kinases Involved in Abnormal Tau Phosphorylation in Alzheimer's Disease" The journal of Biological Chemistry, The American Society for Biochemistry and Molecular Biology, Inc. vol. 276, No. 1, pp 251–260 (2001).

(List continued on next page.)

Primary Examiner—James O. Wilson
Assistant Examiner—Ganapathy Krishnan
(74) Attorney, Agent, or Firm—Winston & Strawn

(57) ABSTRACT

A compound called NATURA, which is a derivative of Isoindigo is useful in aiding the general health of a patient and specifically is beneficial in preventing or treating cancer. This compound and other related Isoindigo, Indigo and Indirubin derivatives are designed such that the bioactivity or bioavailability of the compound is increased. Also, pharmaceutical compositions that include a therapeutically effective amount of at least one of these derivatives and a pharmaceutically acceptable carrier. A method for the use of these pharmaceutical compositions and compounds is taught, wherein a therapeutically effective amount is administered to an animal. The pharmaceutical composition or compound can be re-administered to the animal until a desired treatment or result is accomplished.

9 Claims, 7 Drawing Sheets

OTHER PUBLICATIONS

Hoessel et al., "Indirubin, the active constituent of a Chinese Antileukaemia medicine, inhibits cyclin–dependent kinases", Macmillan Magazines Ltd., Nature Cell Biology, vol. 1, pp. 60–67 (1999).

Xiao M. Liu et al., "Induction of Differentiation and Down–Regulation of c–myb Gene Expression in ML–1 Human Myeloblastic Leukemia Cells by the Clinically Effective Anti–Leukemia Agent Meisoindigo" Chemical Pharmacology, vol. 51, pp. 1545–1551 (1996).

D. Marko et al., "Inhibition of Cyclin–dependent kinase 1 (DCK1) by indirubin derivatives in human tumour cells" Journal of Cancer vol. 84 No. 2, pp 283–289 (2001).

T. Kunikata et al., European Journal of Pharmacology, vol. 410, pp. 93–100 (2000).

* cited by examiner

DERIVATIVE OF ISOINDIGO, INDIGO AND INDIRUBIN FOR THE TREATMENT OF CANCER

TECHNICAL FIELD

The invention relates to new and useful compounds that are derivatives of isoindigo, indigo and indirubin. The invention further relates to the use of these derivatives in the treatment of cancer in animals.

BACKGROUND

Prevention and treatment of cancer has significantly improved in the United States during the past decade because of advancements in epidemiology, the technology of treatment, and the ability to deliver earlier diagnosis. Finding a cure for a diversity of cancers, such as lung, breast, prostate, colon and others however, is still a major challenge. Current approaches for the treatment of cancers are however, still limited to the lengthening of life, or the increase in the quality of life. Additionally, most meaningful therapeutics still have significant side effects. Therefore, it is imperative to find more effective therapeutic agents with lower side effects.

Tumor cells are characterized by uncontrolled cell proliferation due to the loss of the integration and coordination of extracellular signals with the cell cycle machinery. A typical cell cycle is classified into G1, S, G2 and M phases [1–3] and is illustrated in FIG. 2. In mammalian cells, proliferation is controlled in the G1 phase of the cell cycle. At the restriction point, cells can have different destinies. Examples of these cell destinies include: 1) leaving the cell cycle and entering a reversible quiescence phase; 2) exiting cell cycle and undergoing apoptosis; 3) differentiating and irreversibly exiting from the cell cycle; and 4) passing through the restriction point and becoming largely independent of extracellular signals and progress automatically through subsequent cell cycle phases (S, G2, M) to the next G1 phase. A variety of proteins are in turn responsible for the regulated progression of cells through the cell cycle. The key components of cell cycle machinery are the cyclins, the cyclin-dependent kinases (CDKs) and their inhibitors. Cyclins are a remarkably diverse family of proteins, which are synthesized from the mid/late of G1 phase till the M phase of the cell cycle and then rapidly degraded. A CDK typically contains a catalytic domain of 300 amino acids, which is inactive by it self. Cdks become active by binding to a cyclin. Activity of cdks is inhibited by their endogenous inhibitors (cdk inhibitors, or cdkIs include p15/p16/p18/p19 and p21/p27). Specific cyclin/CDK complexes are formed at specific stages of the cell cycle and their activities are required for progression of the cell cycle through S phase and mitosis.

Over-activation of CDKs is a character of a majority of human tumor cells. Strategies have been developed to modulate CDK activity for therapeutic intervention by either directly targeting the catalytic CDK subunit or indirectly affecting the CDK regulatory pathways [3]. Small molecule CDK inhibitors were designed to interact specifically with the ATP binding site of CDKs, such as flavopiridol congeners, polysulfates, toyocamycin derivatives, etc. Anti-cancer effects have been shown in clinical trials for those agents. Modulation of CDK activities can be achieved by regulating phosphorylation of CDKs or altering the expression of the CDKs or the their inhibitors (CKDIs). It is difficult to find specific modulators that do not interfere with other cell cycle components and do not affect normal cells.

A need thus exist for compounds that are easily produced and are highly effective at treating cancer but have minimal toxicity to normal cells.

Many Chinese herbs contain potent anti-cancer chemical components. For example, several Chinese plants such as *Camptotheca acuminata* (camptothecin), Cephalotaxus sp. (homoharringtonine/harringtonine) have provided compounds with significant antitumor activity [6]. PC-SPES, a mixture consisting of extracts from eight herbs for the treatment of prostate cancer, has been demonstrated to have potent anti-androgen activity [7]. Huanglian, a Chinese herbal extract, has recently been shown to inhibit cell growth by suppressing the expression of cyclin B1 and inhibiting CDC2 kinase activity in human cancer cells [8]. In addition, many Chinese herbal products have demonstrated an important role in cancer chemoprevention.

Studies have recently demonstrated that indirubin molecules from the anticancer Chinese herb—Qing Dai, exhibit their anticancer activity through modulating cyclin-dependent kinases [9].

Our previous studies demonstrated that meisoindigo, a second generation of indirubins, arrests leukemia cells at $G_1$ phase, inhibits expression of oncogene c-myb, and induces cell differentiation and maturation at low concentrations (low toxicity) in which cell growth is completely inhibited without a decrease in cell viability [10, 11]. Recent studies demonstrate that indirubin selectively inhibits cyclin-dependent kinases (cdks) by competing with ATP for binding to the catalytic site of the kinase (FIG. 2) [12]. While these compounds have some utility, there still is a need for additional compounds that are effective for such treatments.

SUMMARY OF THE INVENTION

The present invention provides novel derivatives of isoindigo, indigo and indirubin that can be used to treat cancer in animals. These novel compounds exhibit minimal toxicity and side effect with a substantial chemotherapeutic index. These compounds allow for the treatment of a variety of cancers with minimal side affects experienced by the patient. Furthermore, the novel compounds are simple, stable chemical molecules that are substantially easy to produce and administer.

One of the advantages of the present invention is that the novel compounds have an increased solubility and bioavailability compared to the prior art molecules and thus are better suited for the treatment of cancer.

The present invention is directed to a specific group of novel compounds that are derivatives of isoindigo, indigo and indirubin as shown in formulas (I), (II) and (III) respectively

FORMULA (I)

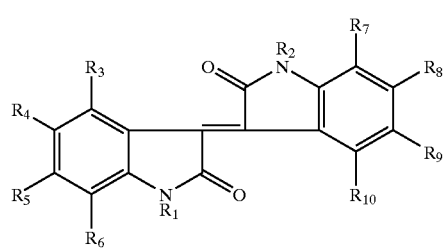

and

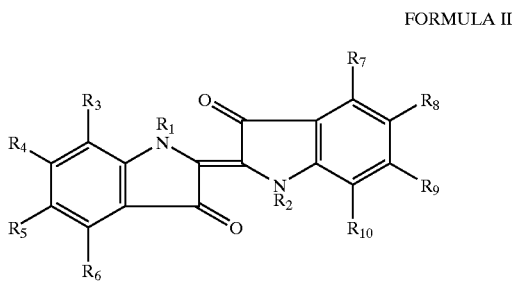

FORMULA II and

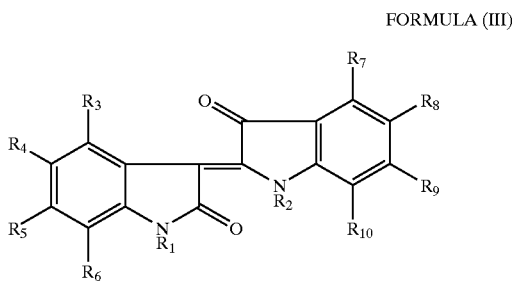

FORMULA (III)

wherein $R_1$, $R_2$, $R_3$, R4, $R_5$, $R_6$, $R_7$, $R_8$, $R_9$, or $R_{10}$ is independently a hydrogen, a monosaccharide, a disaccharide, a halogen, a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfate, sulfonate, sulfonamide or halogens, wherein the hydrocarbyl has 1 to 12 carbon atoms.

A particularly preferred embodiment of the invention, referred to herein as NATURA, is the compound of the following Formula (IV)

FORMULA (IV)

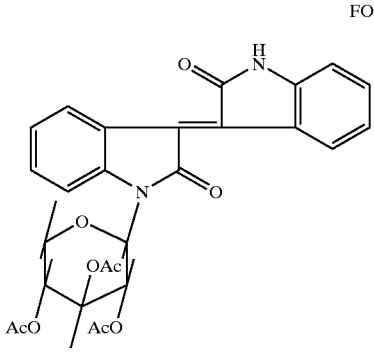

The present invention further provides a method of treating cancer and leukemia comprising administering to the animal a therapeutically effective amount of the novel derivatives of isoindigo and indirubin provided by the invention.

The present invention also provides pharmaceutical compounding that can be used to treat cancer or illnesses in an animal, comprising a therapeutically effective amount of a compound of the invention and a pharmaceutically acceptable carrier.

DETAILED DESCRIPTION OF THE PREFERRED EMBODIMENTS

Figure 1:
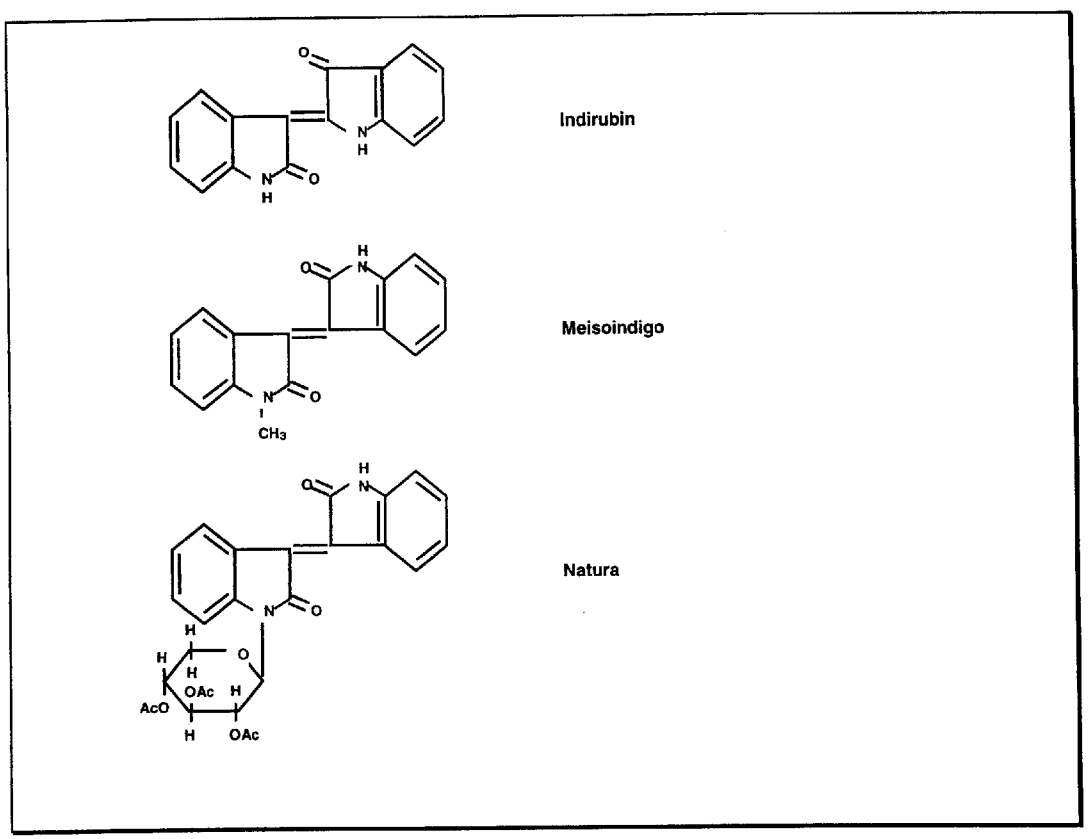
FIG. 1 shows the chemical structures of Indirubin, Meisoindigo, and NATURA, a new chemical entity in accordance with the invention.

The present invention is directed to derivatives of isoindigo, indigo and indirubin that can be used to treat cancer and other illnesses in an animal and also can be used to inhibit activities, which is useful in treating other human disorders, such as Alzheimer's disease, psoriasis, cardiovascular diseases, glomerulonephritis. The examples given below are simply to demonstrate different embodiments of the invention and are not intended in any way to limit the scope of the present invention thereto.

The present invention is directed to a specific group of compounds that are derivatives of isoindigo, indigo, and indirubin as shown in formulas (I), (II), and (III) respectively.

FORMULA (I)

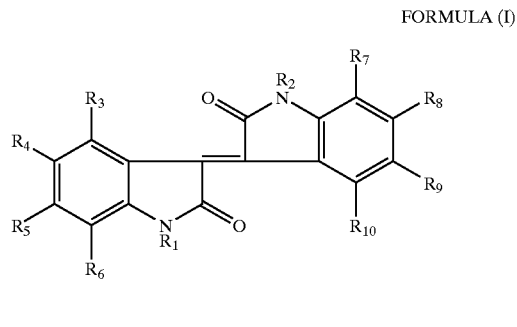

and

FORMULA II

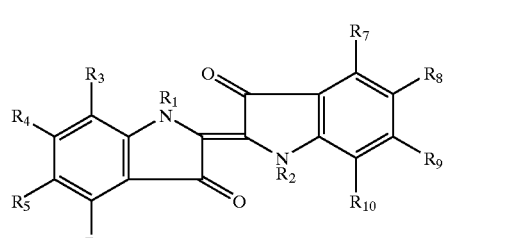

FORMULA (III)

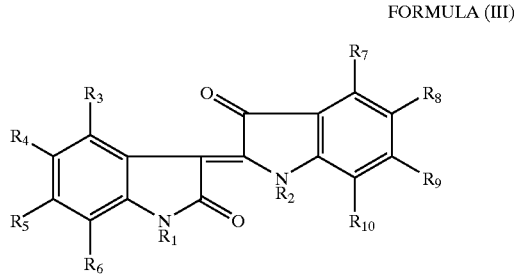

wherein $R_1$, $R_2$, $R_3$, $R_4$, $R_5$, $R_6$, $R_7$, $R_8$, $R_9$, or $R_{10}$ is independently a hydrogen, a monosaccharide, a disaccharide, a halogen, a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfate, sulfonate, sulfonamide or halogens, wherein the hydrocarbyl has 1 to 12 carbon atoms.

Preferred compounds of are those in which at least one $R_1$, $R_2$, $R_3$, $R_4$, $R_5$, $R_6$, $R_7$, $R_8$, $R_9$, or $R_{10}$ is independently a monosaccharide, a disaccharide, or a hydrocarbyl group or a functional hydrocarbyl group substituted with one or more hydroxy moieties, carboxy moieties, nitroxy moieties, monosaccharides, disaccharides, amines, amides, thiols, or halogens, wherein the hydrocarbyl has 1 to 8 carbon atoms; and at least one of $R_1$, $R_2$, $R_3$, $R_4$, $R_5$, $R_6$, $R_7$, $R_8$, $R_9$, or $R_{10}$ enhances the bioactivity or bioavailability of the compound. For example, by mimicking the ribose group of ATP, thus increasing the compounds bioactivity.

It is preferable that $R_1$, $R_2$, $R_3$, $R_4$, $R_5$, $R_6$, $R_7$, $R_8$, $R_9$, or $R_{10}$ enhances the bioactivty or bioavailability of the compound by more closely mimicking the structure of ATP or by increasing the solubility of the compound. It is more preferable that both the bioactivity and bioavailability are increased by one or more of $R_1$, $R_2$, $R_3$, $R_4$, $R_5$, $R_6$, $R_7$, $R_8$, $R_9$, or $R_{10}$.

Additional preferred compounds are those in which either $R_1$ or $R_2$, or both, is independently a monosaccharide, a disaccharide, or a hydrocarbyl group or a functional hydrocarbyl group substituted with one or more hydroxy moieties, carboxy moieties, nitroxy moieties, monosaccharides, disaccharides, amines, amides, thiols, sulfate, sulfonate, sulfonamide, or halogens, and preferably where the hydrocarbyl has 1 to 8 carbon atoms and the functional hydrocarbyl has 1 to 8 carbon atoms and one hydroxyl group for each two carbon atoms. In many cases only one of $R_1$ or $R_2$ needs to be one of the recited moieties, with one of the most preferred substituents being —$CH_2CH_2OH$.

Preferred compounds of Formulas (I), (II), and (III) are ones in which $R_1$ or $R_2$ are a glucose molecule.

The most preferred compound is called NATURA and has Formula (IV)

FORMULA (IV)

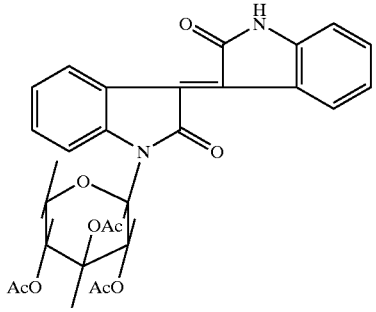

The following lists are not intended to be all encompassing, but simply demonstrative. The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 12 carbon atoms. The preferred embodiments include those in which the hydrobcarbyl group has 1 to 8 carbon atoms. These and other hydrocarbyl groups may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal "reactive" and/or "latent reactive" functionality and/or leaving groups. Reactive functionality refers to functionality which is reactive with common monomer/polymer functionality under normal conditions well understood by those persons of ordinary skill in the relevant art. As examples of reactive functionality may be mentioned active hydrogen containing groups such as hydroxyl, amino, carboxyl, thio, amido, carbamoyl and activated methylene; isocyanato; cyano; epoxy; ethylenically unsaturated groups such as allyl and methallyl; and activated unsaturated groups such acryloyl and methacryloyl, and maleate and maleimido (including the Diels-Alder adducts thereof with dienes such as butadiene). Latent reactive functionality within the meaning of the present invention and, as would clearly be understood by those persons of ordinary skill in the relevant art, refers to reactive functionality which is blocked or masked to prevent premature reaction. As examples of latent reactive functionality may be mentioned ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention and, as would clearly be understood by those persons of ordinary skill in the relevant art, is a substituent attached to the hydrocarbyl chain or ring which during reaction is displaced to create a valency on a carbon or hetero atom in the hydrocarbyl chain or ring. As examples of leaving groups may be mentioned halogen atoms such as chlorine, bromine and iodine; quaternary ammonium salts; sulfonium salts; and sulfonates.

A monosaccharide or disaccharide of the present invention is preferably glucose, fructose, ribulose, galactose, mannose, cellobiose, allose, altrose, ribose, xylose, arabinose, sucrose, and lactose. Preferably D-glucose, D-ribose, D-glacatose, D-lactose and D-sucrose.

The term "halogen" indicates fluorine, chlorine, bromine, or iodine. Preferred are fluorine or chlorine.

As used herein, amino acid means an L- or D-amino acid (or a residue thereof), preferably L-, selected from the group consisting of alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine, or valine. The term peptide is two or more amino acids joined by a peptide bond, preferably containing 2 to 8 amino acids, and more preferably containing 2 to 6 amino acids.

The present invention also provides a therapeutic method for treating an animal with cancer comprising administering to an animal a therapeutically effective of the compounds described above. The invention may also be used to prevent cancer. The compounds disclosed herein play a role in chemoprevention. The compounds can be used to prevent cancer by acting as cdk inhibitors, that block cancer from progressing (second step in the carcinogenesis), thus preventing its occurrence.

The invention may be used to an animal with cancer, wherein it is preferable that the animal is a mammal and more preferable that the animal is human. Furthermore, it is believed that the invention can be used to treat any type of cancer, and data is provided herein to demonstrate effectiveness for colon cancer, hormone dependent and independent prostate cancer, breast cancer, and leukemia.

It should also be noted that therapeutic benefits may be realized by the administration of at least two, three or more of the compounds concurrently or sequentially. The compounds may also be combined with other therapies to provide combined therapeutically effective amounts. The compound can be administered, for example, in combination with additional agents selected from the group consisting of radiotherapeutic agents, hormonal therapy agents, immunotherapeutic agents, chemotherapeutic agents, cryotherapeutic agents and gene therapy agents.

The present invention further provides a pharmaceutical composition for treating cancer in an animal comprising a therapeutically effective amount of a derivative of isoindigo or indirubin or combination of derivatives and a pharmaceutically acceptable carrier. This can take a variety of forms adapted to the chosen route of administration as discussed above.

Those skilled in the art will recognize various synthetic methodologies that may be employed to prepare non-toxic pharmaceutically acceptable compositions of the compounds encompassed by Formulas I, II and III. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formulas I, II and III may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formulas I, II and III and a pharmaceutically acceptable carrier. One or more compounds of general Formulas I, II and III may be present in association with one or more non-toxic pharmaceutically acceptable carriers and/or diluents and/or adjuvants and if desired other active ingredients. The pharmaceutical compositions containing compounds of general Formulas I, II and III may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulas I, II and III may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formulas I, II and III may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the compound or a composition containing the compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water.

Dosage levels of the order of from about 0.01 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels laboratory animals that receive the compound intravenously.

Serum protein binding may be predicted from albumin binding assays. Such assays are described in a review by Oravcova, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

The amount of the composition required for use in treatment will vary not only with the particular compound selected but also with the route of administration, the nature of the condition being treated and the age and condition of the patient and will be ultimately at the discretion of the attendant physician or clinician.

EXAMPLES

Examples of the compounds of Formulas I–IV and their uses to treat cancer are described in the following Examples.

A number of indirubin derivatives were designed and screened for their Anti-cancer activities. Among the derivatives screened, 1-(β-D-O-Triacetyl-xylopransyl)-isoindigo, with chemical formula $C_{27}H_{24}N_2O_9$ (NATURA, see chemical structure in FIG. 1) has been found to be the most active against not only leukemia, but also various human cancer cells with lower toxicity effects.

Reagents: Meisoindigo and NATURA were synthesized in our laboratory, purified by HPLC (high performance liquid chromatography) with a purity of 99.5%. NATURA is reddish crystal, with a molecular weight of 520. It was prepared in DMSO, and stored under minus 20° C. Retinoid Acid, daunomycin, paclitaxel were obtained from Sigma Chemical Company (St. Louis, Mo.), Casodex and Proscar were gifts from Dr. W. Kreis (New York). NS389 was purchased from Biomol Research Labs, Inc. Other chemicals including agents for MTT were purchased from Sigma.

Cell Cultures: Human cancer cell lines of breast (MCF-7 and SKBR-3), colon (LOVO and DLD-1), prostate (LNCaP, DU 145 and PC-3), and human epithelial cell line HUVEC were purchased from American Type Culture Collection (Rockville, Md.). The cells were maintained according to manufacture's instructions.

Assay for cyclin dependent kinase activity: HUVEC and LNCaP cells were cultured in EMB (endothelial cell basal medium) and RPMI 1640 containing 10% FBS, respectively. The cells grown exponentially were exposed to indicated concentrations of meisoindigo or NATURA for 24 hr. The cells were harvested, washed, and total proteins extracted as described previously [13]. One hundred $\mu$g of the proteins were immuno-precipitated using antibodies against either cdk4/6 or cyclin D1 overnight at 4° C. in the presence of a cocktail of protease inhibitors. The immuno-precipitates were washed 4 times with protein extraction buffer and once with kinase assay buffer, and reacted with 75 $\mu$g/ml histone H1 in the presence of [$\gamma$-$^{32}$P]-ATP. The phosphorylated histone H1 (represent cdk activity) was measured by scintillation counting or by SDS-polyacrylaimde gel electrophoresis [14, 15].

It was observed that this agent strongly inhibits cyclin D mediated CDK activities and cell growth of various types of human cancer cells including cancer cell lines of breast, prostate, colon and lung ($IC_{50}$ are between 1.5 to 9.0 $\mu$M). Both Meisoindigo and NATURA also exhibit very low toxicity with $LD_{50}$ in mice. The test data below is for Meisoindigo 3.9±0.8 g/kg, and for NATURA 7.33±1.15 g/kg as compared to a value for Cisplatin of 15.9±1.3 mg/kg under the same experimental conditions.

It was found that at higher concentrations, Meisonindigo blocks tumor cells at G2+ M phase at the second check point, allowing the targeting of those cancer cells that escape from treatments at the earlier stage of the cycle. At low concentrations, Meisoindigo inhibits cyclin-D mediated cdk activity, and at higher concentration, it interferes with both cyclin A and/or B mediated cdk activity.

Figure 2:
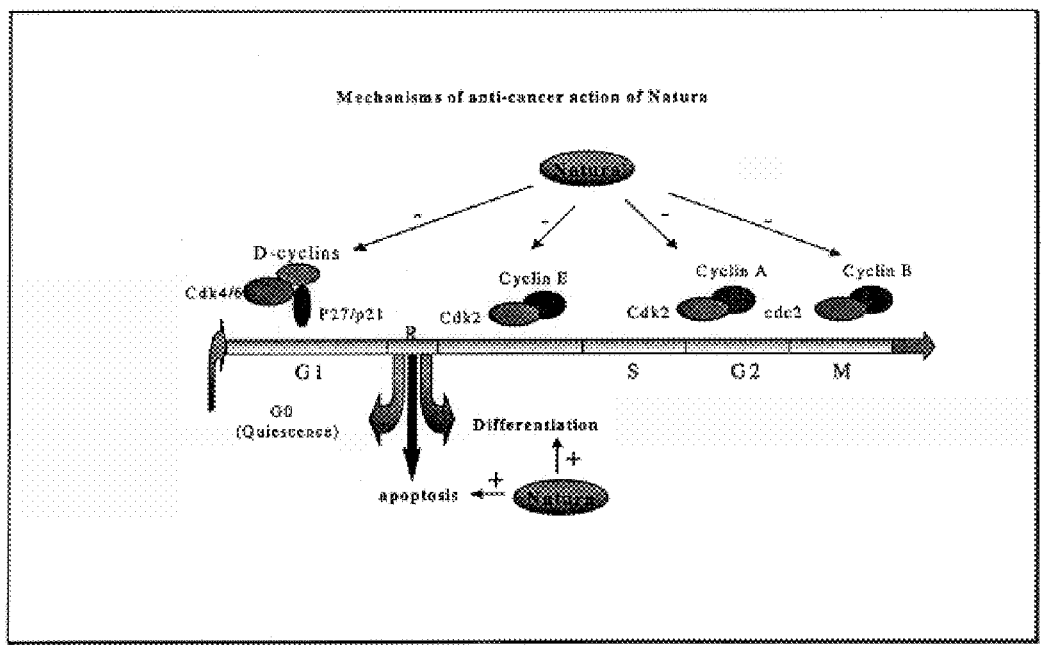
FIG. 2 shows a model of anticancer mechanisms of derivatives of isoindigo and indirubin.

FIG. 2 shows a model of anticancer mechanisms of NATURA. A typical cell cycle is classified into G1, S, G2 and M phases. R: the restriction point, at this point, cells can have different destinies: 1) To leave the cell cycle and enter a reversible quiescence phase, $G_0$, phase; 2) To exit cell cycle and undergo apoptosis; 3) To differentiate and irreversibly exit from the cell cycle, and 4) To pass through the restriction point and then become largely independent of extracellular signals and progress automatically through subsequent cell cycle phases (S, G2, M) to the next G1 phase. A variety of proteins are in turn responsible for the regulating progression of cells through the cell cycle. The key components of cell cycle machinery are the cyclins (D cyclins, cyclin A, cyclin B and cyclin E), the cyclin-dependent kinases (CDKs, cdk4/6, cdk2, and cdc2) and their inhibitors (p15/p16/p18/19, p21/p27). Meisoindigo and NATURA specifically inhibit activities of cdk4/6, cdk2, and cdc2, thus against cell proliferation. Those compounds have also showed to induce cell differentiation/maturation without affecting cell viability, and promoter apoptosis. −: inhibits, and +: induce or promote the activity.

Example 1

Anticancer Activities of NATURA in Vitro by MTT

Growth inhibitory effects of NATURA and other agents on human cancer cells were determined by standard MTT (3-(4,5-dimethylthiazol-2-yl)-2.,5-diphenyltetrazolium bromide Test) as described previously [16]. Briefly, cancer cells grown exponentially were aliquoted into 96-well plates at a density of 5000 cells /200 $\mu$l per well in RPMI 1640 medium containing 10% FBS overnight. The cells in the plates were then exposed to series of dilution of indicated agent. After 72 h of incubation, 100 $\mu$l of the medium was removed from each of the wells and 50 $\mu$l of a 1 mg/ml solution of 3-(4,5-dimethylthiazol-2-yl)-2.,5-diphenyltetrazolium bromide (MTT) was added to each well and the cells were incubated for additional 4 h. 200 $\mu$l of solution of 0.04 N HCl-isopropanol was added to each well to dissolve the black fromazan participates, and absorbance at 540 nm was measured on a 96-Well.

Effects of NATURA on Human Cancer Cells

A good response of different types of human cancer cells to the treatment of Meisoindigo and NATURA was obtained by MTT after three day exposure, including cancer cell lines of breast (MCF-7 and SKBR-3, Table 1); colon (LOVO and DLD-1, Table 2), and hormone dependent and independent prostate (LNCaP, PC-3 and DU145, Table 3). As shown in Table 1–3, the growth inhibitory effects of Meisoindigo (IC50 2.15 to 8.31 $\mu$M) on all of those tested human cancer cell lines are much stronger than retinoid acid (IC50 21.45 to >50 $\mu$M), a differentiation inducer, and NS389 (IC50 >200 $\mu$M), a new developed Cox 2 inhibitor. The anticancer activity of Based on IC50 of NATURA (IC50 from 1.64 to 6.92 $\mu$M), the anticancer activities of NATURA is slightly stronger than its parental compound Meisoindigo (IC50 2.1 to 8.3 $\mu$M). We expect that a much stronger anticancer activity of NATURA than Meisoindigo will occur in vivo due to a significant improvement of its bioavailability by increasing its solubility. Similar results for all of these tests were also obtained using SRB (sulforhodarnine B, data not shown). The activities of NATURA against both hormone dependent and independent prostate cancers are also much stronger than that of clinical current hormone therapeutic agents, Casodex and Proscar (Table 3). No significant differences of those cancer cells in response to the treatment of Meisoindigo and NATURA were observed whereas cancer cells of breast and colon seem more sensitive than that of prostate (Table 3) in response to the treatment of Daunomycin. These data support that Meisoindigo and NATURA are against a common target of cancer cells, i.e. cyclin dependent kinases, thus it will be proven to be a useful chemotherapeutic agent for the treatment of various types of human solid tumors. Although the anticancer effect of Meisoindigo and NATURA are weaker than that of daunomycin or paclitaxel in vitro assay, it is noted that the toxicities of Meisoindigo and NATURA may much lower than those of agents as implicated by their LD50 (3.90±0.8 g/kg for Meisoindigo and 7.33±1.15 g/kg for NATURA in mice).

TABLE 1

Comparison of IC50 (μM) of Meisoindigo and NATURA with Chemotherapeutic Agents Against Breast Cancer Cell Lines by MTT

| | CELL LINE | |
|---|---|---|
| Agent | MCF-7 | SKBR-3 |
| Meisoindigo | 4.37 ± 0.31 | 2.17 ± 0.17 |
| NATURA | 2.91 ± 0.28 | 1.71 ± 0.14 |
| Daunomycin | 0.054 ± 0.011 | 0.061 ± 0.0051 |
| Retinoid | 21.45 ± 3.78 | >50 |
| NS389 | >200 | >200 |

TABLE 2

Comparison of IC50 (μM) of NATURA with Chemotherapeutic Agents Against Colon Cancer Cells by MTT

| | CELL LINE | |
|---|---|---|
| Agent | LOVO | DLD-1 |
| Meisoindigo | 5.76 ± 0.72 | 2.15 ± 0.17 |
| NATURA | 4.31 ± 0.59 | 1.64 ± 0.181 |
| Daunomycin | 0.035 ± 0.004 | 0.094 ± 0.0130 |
| Retinoid Acid | 75.34 ± 12.49 | 49.70 ± 5.72 |
| Paclitaxel | 0.00364 ± 0.00051 | 0.00315 ± 0.00037 |
| NS389 | >200 | >200 |

TABLE 3

Comparison of IC50 (μM) between Meisoindigo, NATURA and Chemotherapeutic Agents against Prostate Cancer Cell Lines.

| | CELL LINE | | |
|---|---|---|---|
| Agent | LNCaP | PC-3 | DU145 |
| Meisoindigo | 2.34 ± 0.33 | 3.26 ± 0.51 | 8.31 ± 0.93 |
| NATURA | 1.72 ± 0.27 | 2.41 ± 0.39 | 6.92 ± 0.73 |
| Daunomycin | N/A | 0.24 ± 0.018 | 0.107 ± 0.004 |
| Retinoid Acid | 15.95 ± 3.19 | >50 | >50 |
| NS389 | 65.54 ± 9.46 | >200 | >200 |
| Proscar | 40.60 ± 7.12 | 133.68 ± 12.94 | N/A |
| Casodex | 57.40 ± 7.21 | 120.11 ± 17.31 | N/A |

Figure 3:
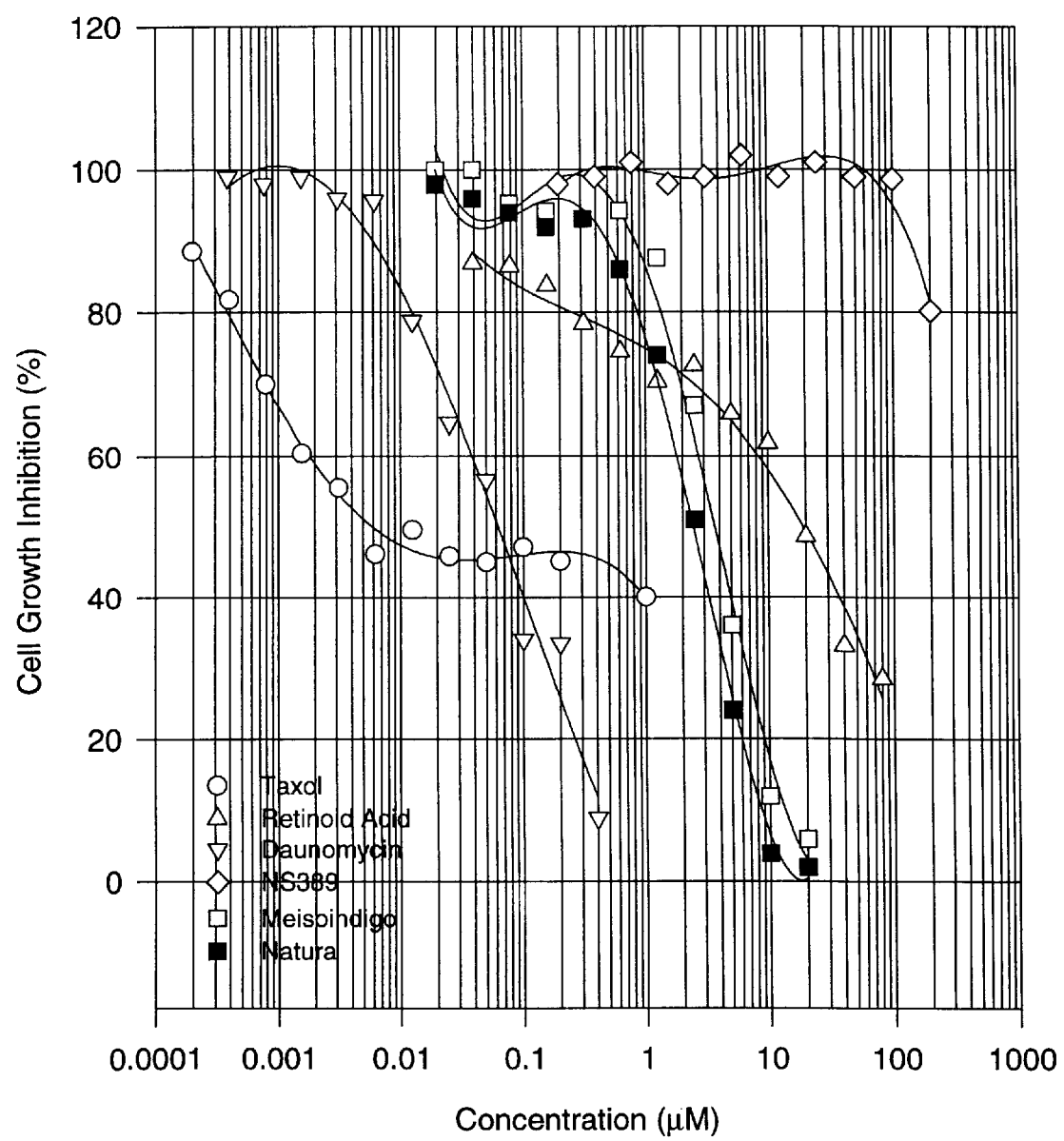
FIG. 3 is a graph of anticancer affects of NATURA in MCF-7 breast cancer cells.
Figure 4:
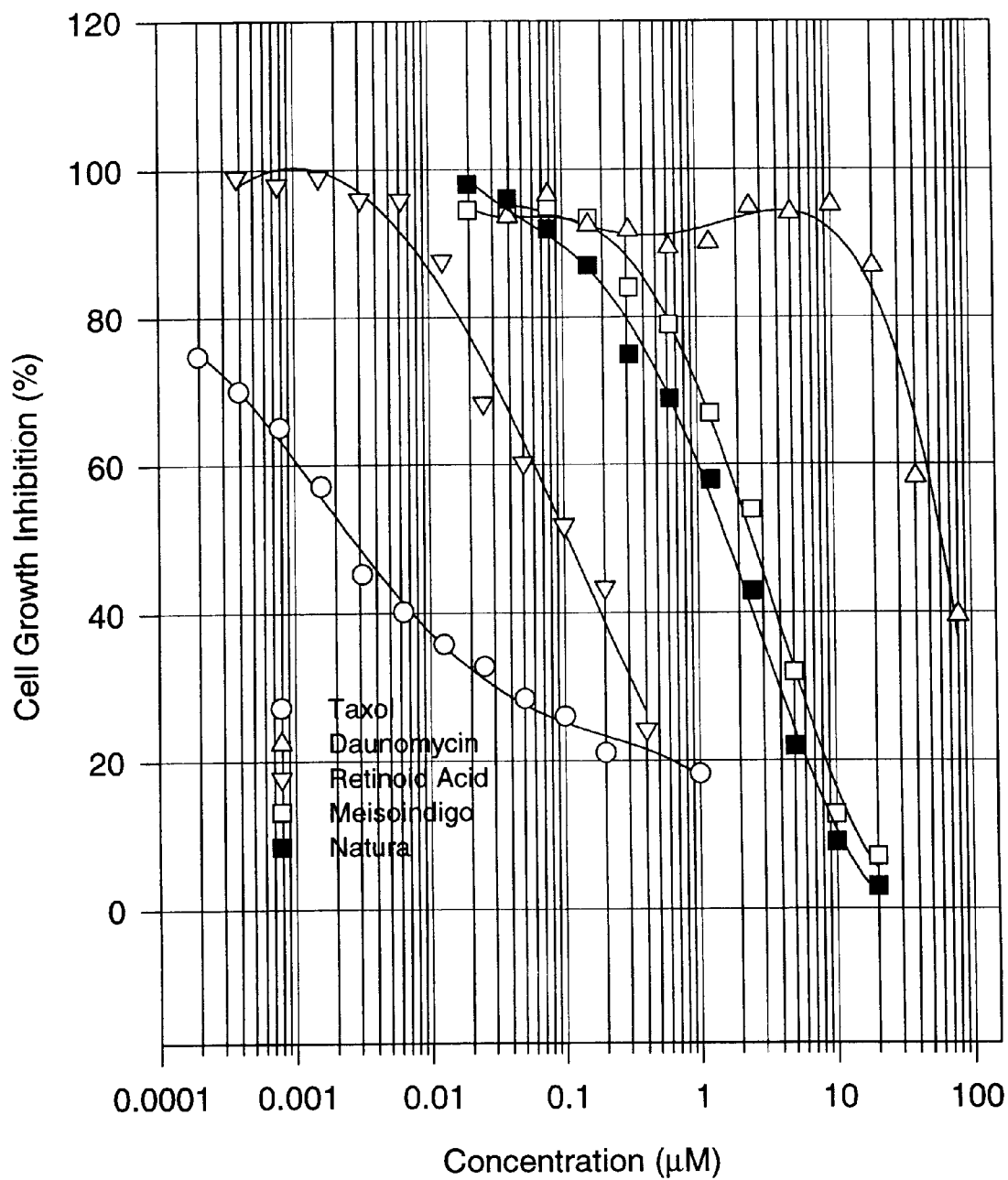
FIG. 4 is a graph of the anti-cancer activity of NATURA in DLD-1 colon cancer cells.
Figure 5:
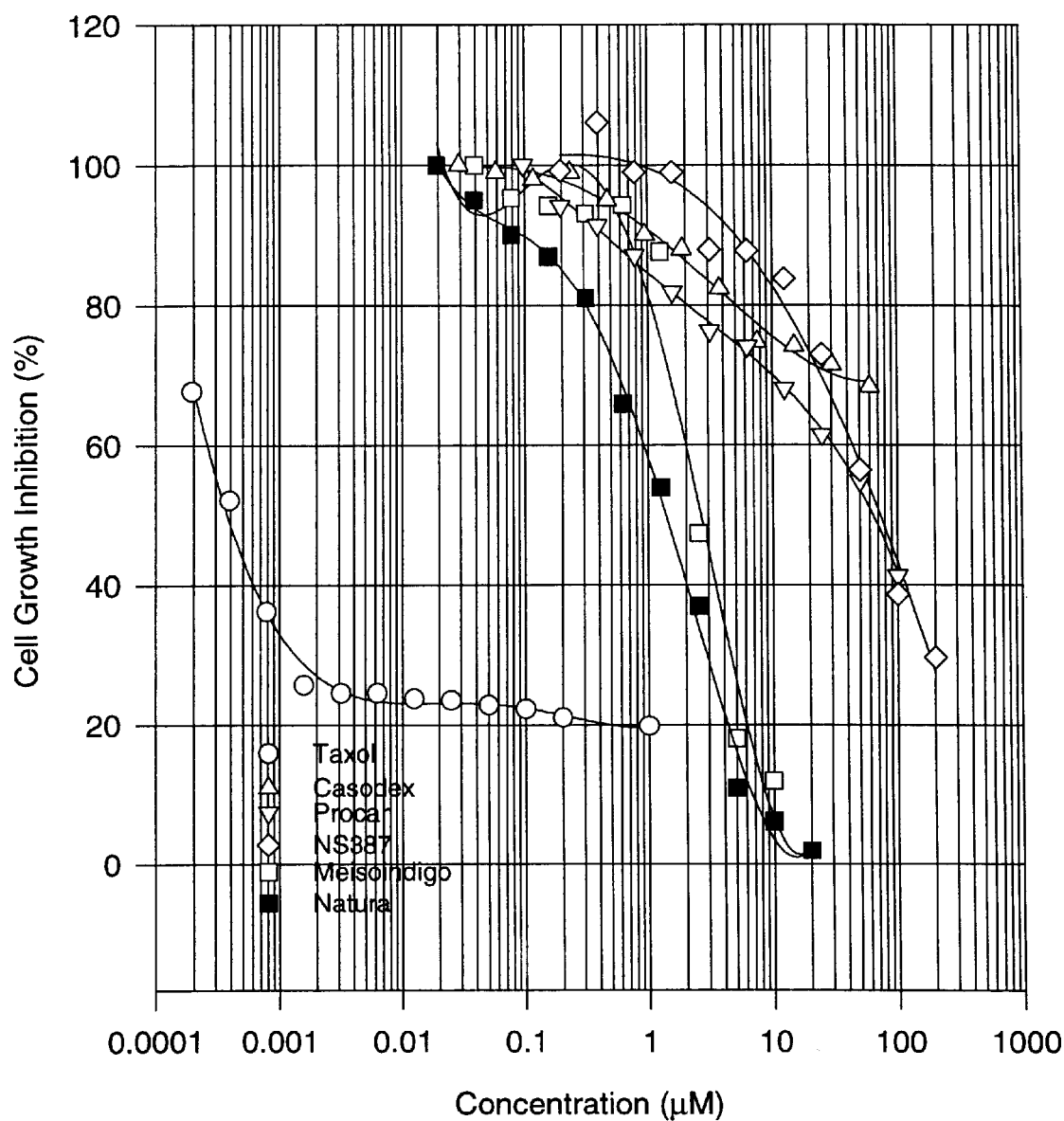
FIG. 5 is a graph of the anti-cancer activity of NATURA in LNCaP hormone-dependent prostate cancer cells.

FIGS. 3–5 show the anticancer affects of NATURA in MCF-7 breast cancer cells, DLD-1 colon cancer cells, and LNCaP hormone-dependent prostate cancer cells. The cancer cells grown exponentially were aliquoted into 96-well plates at a density of 5000 cells /200 μl per well in RPMI 1640 medium containing 10% fetal bovine serum (FBS) overnight. The cells in the plates were then exposed to series of dilution of indicated agent. After 72 h of incubation, 100 μl of the medium was removed from each of the wells and 50 μl of a 1 mg/ml solution of 3-(4,5-dimethylthiazol-2-yl)-2.,5-diphenyltetrazolium bromide (MTT) was added to each well and the cells were incubated for additional 4 h. 200 μl of solution of 0.04 N HCl-isopropanol was added to each well to dissolve the black fromazan participates, and absorbance at 540 nm was measured on a 96-Well Microplate Reader [16]. Each experiment was repeated at least three times.

Figure 6:
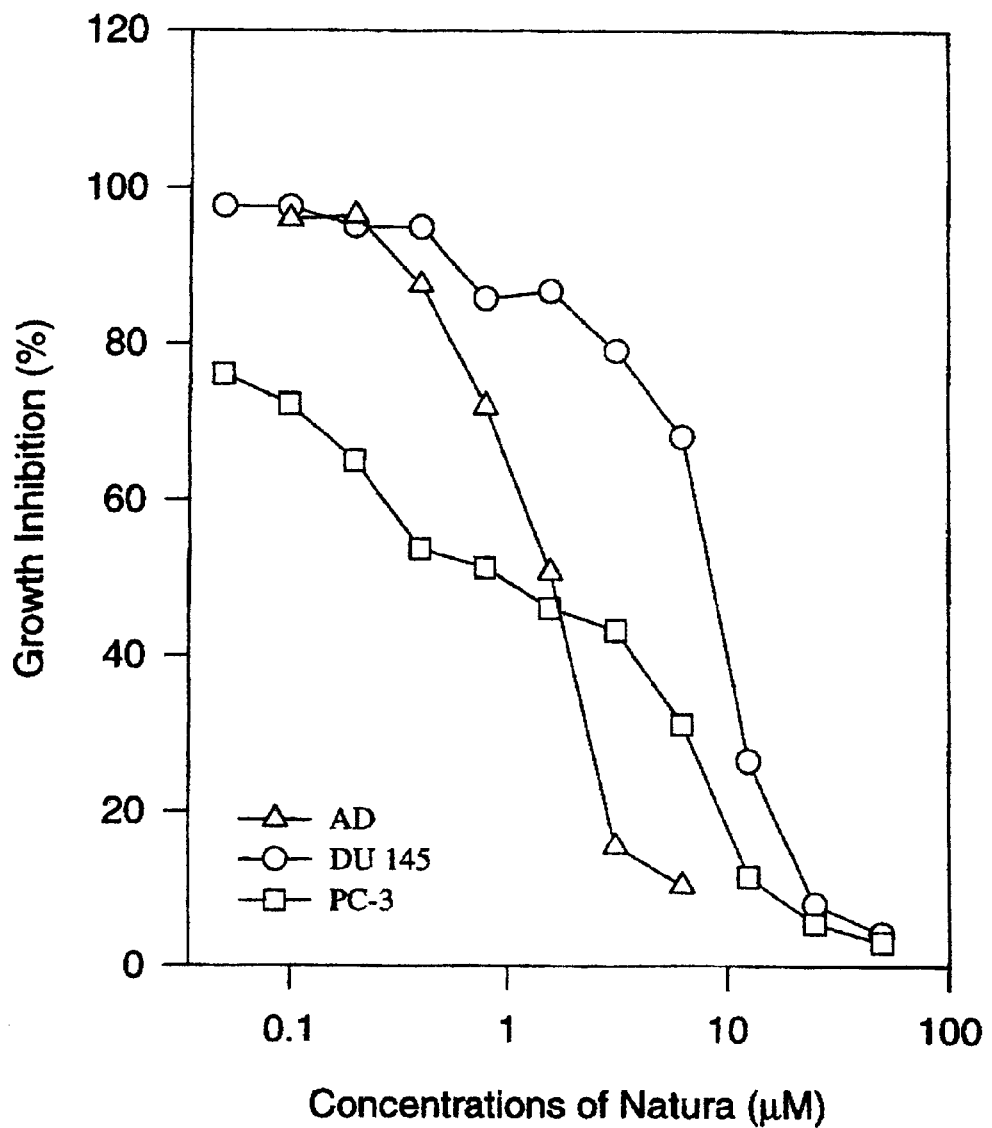
FIG. 6 is a graph of the effects of NATURA on hormone dependent and independent prostate cancer cell growth.
Figure 7:
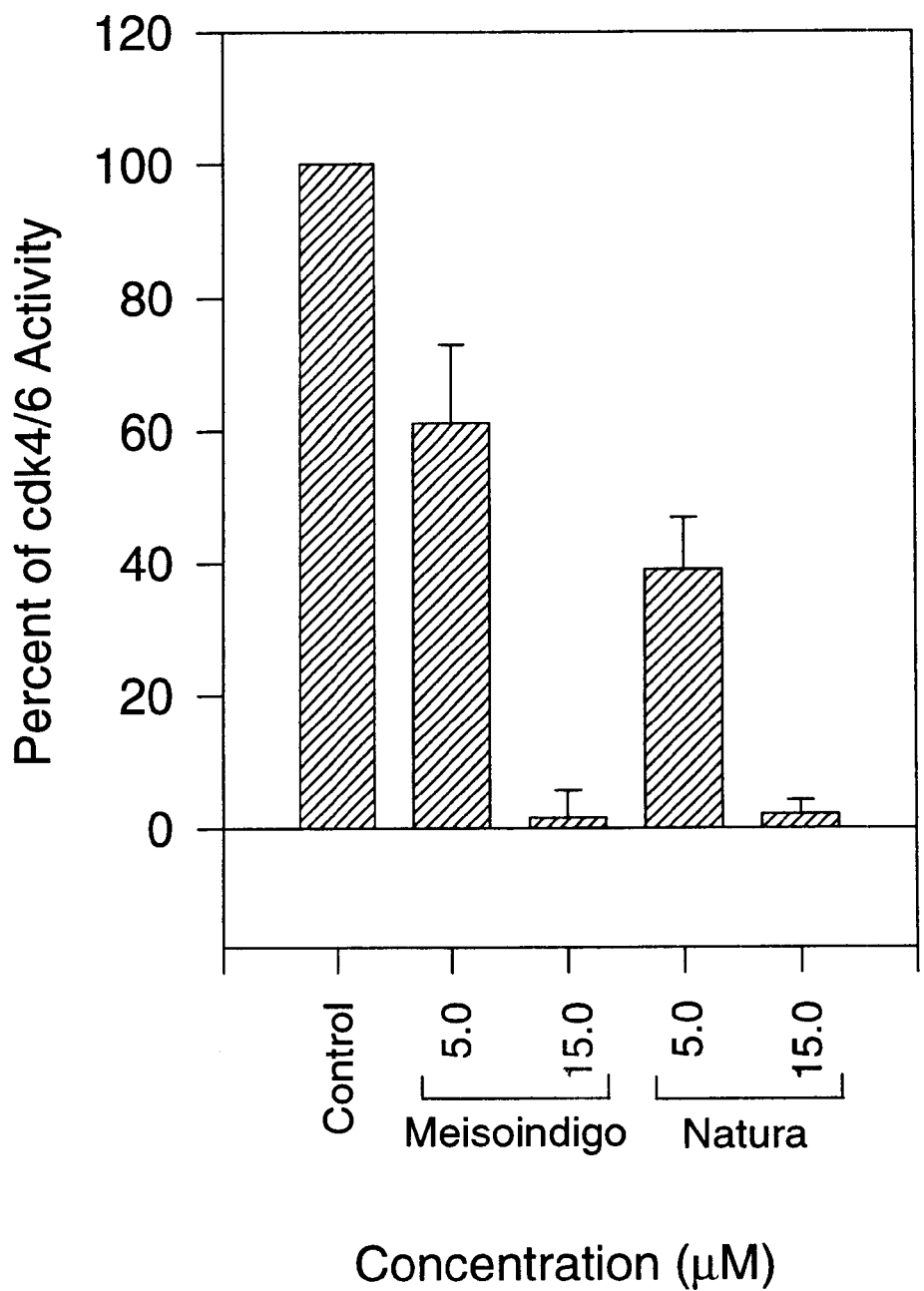
FIG. 7 is a graph of the inhibitory compound NATURA on cdk4/6 activity.

FIG. 6 shows the anticancer affects of NATURA in hormone dependent and independent prostate cancer cells. HVEC and LNCaP cells were cultured in EMB (endothelial cell basal medium) and RPMI 1640 containing 10% FBS, respectively. The cells grown exponentially were exposed to indicated concentrations of meisoindigo or NATURA for 24 hr. The cells were harvested, washed, and total proteins extracted as described previously [13]. One hundred μg of the proteins were immuno-precipitated using antibodies against either cdk4/6 or cyclin D1 overnight at 4° C. in the presence of a cocktail of protease inhibitors. The immuno-precipitates were washed 4 times with protein extraction buffer and once with kinase assay buffer, and reacted with 75 μg/ml histone H1 in the presence of [γ-$^{32}$P]-ATP. The phosphorylated histone H1 (represent cdk activity) was measured by scintillation counting.

Example 2

Anticancer Activity in Animal Models

Two established animal cancer models, Lewis lung carcinoma, and Walker 256 sarcoma [17–20], have been used to evaluate anti-solid tumor activities of meisoindigo and NATURA as described previously. Briefly, C57 mice, body weight between 18 to 22 grams, and rat, body weight between 50 to 55 grams, were randomly divided into several groups, ten of each, respectively. Approximately 2×10$^6$ of Lewis cancer cells or Walker sarcoma cells were transplanted into mice or rat. Twenty-four hrs after the transplantation, equal molar dosages of indirubin, and meisoindigo were given orally for 10 days. The animals in the control group were given 0.1 ml saline (drug vehicle, negative control) for the same periods of time as treated group. The animals at end of the treatment were sacrificed and tumors were removed and weighed.

Anticancer Activities of Meisoindigo in vivo

As shown in Table 4, Meisoindigo showed significant anticancer activities for both Lewis Lung cancer and Walker 256 sarcoma and the activities were much stringer than that of its parental compound indirubin.

TABLE 4

Anti-cancer activities of Meisoindigo and NATURA in animals.

| Tumor | Group | Dose (mg/kg × d) | No. of animals | Tumor Size X ± SD | Inhibition (%) | Statistic (ST test) |
|---|---|---|---|---|---|---|
| Lewis Lung Cancer | Control | — | 10 | 3.5 ± 0.44 | 0 | |
| | Indirubin | 100 × 9 | 10 | 2.58 ± 0.21 | 26.3 ± 2.8 | P < 0.05 |
| | Meisoindigo | 106 × 9 | 10 | 1.80 ± 0.15 | 48.6 ± 4.1 | P < 0.01 |
| Walker 256 | Control | — | 10 | 9.7 ± 1.02 | 0 | |
| | Indirubin | 100 × 9 | 10 | 3.94 ± 0.71 | 59.4 ± 2.9 | P < 0.01 |
| | Meisoingo | 106 × 9 | 10 | 2.10 ± 0.17 | 71.6 ± 3.1 | P < 0.01 |

Previous studies have shown that Meisoindigo induce ML-1 cell differentiation and maturation while suppresses the expression of oncogene c-myb, and arrests the cancer cells at G1 phase [11]. Recently study has been shown that myb activation is liked to the phosphorylation mediated by cyclin dependent kinases, and suppress of cyclin D and its kinase activity have been indicated to play a role induction of cell differentiation. In this preliminary observation, we further confirmed both Meisoindigo and NATURA strongly suppress D cyclins mediated cdk4/6 activity (FIGS. 2, and 3). Over 56% of the enzyme activity was inhibited by 5.0 $\mu$M and completely inhibition was achieved when LNCaP prostate cancer cells were exposed to 15 $\mu$M of either Meisoindigo or NATURA for 24 h. Similar results were also obtained in human epithelial cell line HUVEC cells (data not shown), indicating the Meisoindigo and NATURA may also have anti-angiogensis activity.

These analyses indicate that Meisoindigo and NATURA is an attractive potential therapeutic agent against various types of human cancers as it specifically targeting cyclin dependent kinases. IC50 of NATURA for all tested human cancer cell lines was found to be between approximately 1.64 to 6.92 $\mu$M, an effective range as shown by many clinical therapeutic agents. Meisoindigo has already showed strong anticancer activities in animals.

The stable and simple chemical structures of these compounds makes them easy to synthesize and administer. Moreover, they possess new chemical structures that exhibit anticancer activity, which can be used as a chemotherapeutic agents alone or in combination with other conventional agents for the treatment of various types of cancer with enhanced results.

For example, cancer patients undergoing chemotherapy often experience hair loss. Although temporary, this effect is emotionally distressing, a constant visual reminder of the individual's condition. Many anti-cancer drugs that lead to CIA target specific phases of the cell cycle. As a result, they prove selectively toxic to cells undergoing division. The epithelium of the hair follicle is particularly sensitive to these effects because it divides so rapidly. It is known that the inhibition of cell cycle progression diminishes the toxicity of the drugs. Accordingly, the combination of NATURA taken orally, at low dosage so that it has very low toxicity, would be beneficial in reducing the extent of hair loss in patients undergoing treatment for such situations. In addition, the amount of conventional chemotherapy agent would be reduced, in turn further reducing the extent of hair loss in the patient. Thus, the combination of NATURA with a conventional cancer treatment agent will result in similar treatment efficacies with less side effects than in conventional chemotherapy.

References

1. Morgan, D. O., Principles of CDK regulation. Nature, 1995. 374(6518): p. 131–4.
2. Buolamwini, J. K., Cell cycle molecular targets in novel anticancer drug discovery. Curr Pharmn Des, 2000. 6(4): p. 379–92.
3. Senderowicz, A. M., Development of cyclin-dependent kinase modulators as novel therapeutic approaches for hematological malignancies. Leukemia, 2001. 15(1): p. 1–9.
4. Buchdunger, E., A. Matter, and B. J. Druker, Bcr-Abl inhibition as a modality of CML therapeutics. Biochim Biophys Acta, 2001. 1551(1): p. M11–8.
5. Druker, B. J., et al., Activity of a specific inhibitor of the BCR-ABL tyrosine kinase in the blast crisis of chronic myeloid leukemia and acute lymphoblastic leukemia with the Philadelphia chromosome. N Engl J Med, 2001. 344(14): p. 1038–42.
6. Han, J., Traditional Chinese medicine and the search for new antineoplastic drugs. J Ethnopharmacol, 1988. 24(1): p. 1–17.
7. DiPaola, R. S., et al., Clinical and biologic activity of an estrogenic herbal combination (PC-SPES) in prostate cancer. N Engl J Med, 1998. 339(12): p. 785–91.
8. Li, X. K., et al., Huanglian, A chinese herbal extract, inhibits cell growth by suppressing the expression of cyclin B1 and inhibiting CDC2 kinase activity in human cancer cells. Mol Pharmacol, 2000. 58(6): p. 1287–93.
9. Damiens, E., et al., Anti-mitotic properties of indirubin-3'-monoxime, a CDK/GSK-3 inhibitor: induction of endoreplication following prophase arrest. Oncogene, 2001. 20(29): p. 3786–97.
10. Ji, X. J., et al., Pharmacological studies of meisoindigo: absorption and mechanism of action. Biomed Environ Sci, 1991. 4(3): p. 332–7.
11. Liu, X. M., et al., Induction of differentiation and down-regulation of c-myb gene expression in ML-1 human myeloblastic leukemia cells by the clinically effective anti-leukemia agent meisoindigo. Biochem Pharmacol, 1996. 51(11): p. 1545–51.
12. Marko, D., et al., Inhibition of cyclin-dependent kinase 1 (CDK1) by indirubin derivatives in human tumour cells. Br J Cancer, 2001. 84(2): p. 283–9.
13. Wang, L. G., et al., Down-regulation of prostate-specific antigen expression by finasteride through inhibition of complex formation between androgen receptor and steroid receptor-binding consensus in the promoter of the PSA gene in LNCaP cells. Cancer Res, 1997. 57(4): p. 714–9.
14. Wang, L. G., et al., Activation of casein kinase II in ML-1 human myeloblastic leukemia cells requires IGF-1 and transferrin. J Leukoc Biol, 1995. 57(2): p. 332–4.
15. Kong, M., et al., Cyclin F regulates the nuclear localization of cyclin B1 through a cyclin-cyclin interaction. Embo J, 2000. 19(6): p. 1378–88.
16. Kreis, W., D. R. Budman, and A. Calabro, Unique synergism or antagonism of combinations of chemotherapeutic and hormonal agents in human prostate cancer cell lines. Br J Urol, 1997. 79(2): p. 196–202.
17. Yamaura, T., et al., Model for mediastinal lymph node metastasis produced by orthotopic intrapulmonary implantation of lung cancer cells in mice. Hum Cell, 1999. 12(4): p. 197–204.
18. Mitani, N., et al., Inhibitory effect of berberine on the mediastinal lymph node metastasis produced by orthotopic implantation of Lewis lung carcinoma. Cancer Lett, 2001. 165(1): p. 35–42.
19. Freitas, J. J., et al., Walker-256 tumor growth causes oxidative stress in rat brain. J Neurochem, 2001. 77(2): p. 655–63.
20. Wicki, A. and V. Niggli, The Rho/Rho-kinase and the phosphatidylinositol 3-kinase pathways are essential for spontaneous locomotion of Walker 256 carcinosarcoma cells. Int J Cancer, 2001. 91(6): p. 763–71.
21. Gianni, L., et al., Nonlinear pharmacokinetics and metabolism of paclitaxel and its pharmacokinetic/pharmacodynamic relationships in humans. J Clin Oncol, 1995. 13(1): p. 180–90.
22. Ohtsu, T., et al., Clinical pharmacokinetics and pharmacodynamics of paclitaxel: a 3-hour infusion versus a 24-hour infusion. Clin Cancer Res, 1995. 1(6): p. 599–606.

23. Huizing, M. T., et al., Pharmacokinetics of paclitaxel and metabolites in a randomized comparative study in platinum-pretreated ovarian cancer patients. J Clin Oncol, 1993. 11(11): p. 2127–35.

What is claimed is:

1. A compound having the following chemical structure:

Formula (IV)

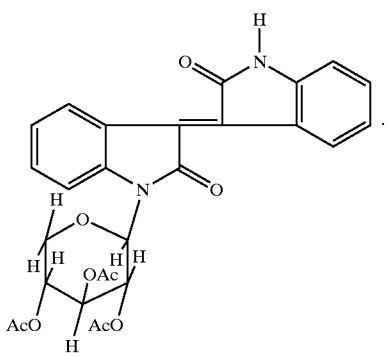

2. A method for treatment of cancer, comprising administering a therapeutically effective amount of a compound having the following chemical structure:

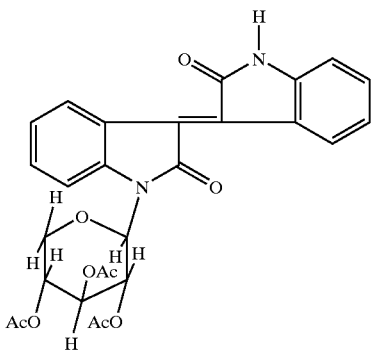

to an animal.

3. The method of claim 2, wherein said animal is a human.

4. The method of claim 2, wherein the compound is administered in combination with an additional agent selected from the group consisting of radiotherapeutic agents, hormonal therapy agents, immunotherapeutic agents, chemotherapeutic agents, cryotherapeutic agents and gene therapy agents.

5. The method of claim 2, wherein the compound is administered orally.

6. The method of claim 2, wherein the cancer is selected from colon cancer and hormone dependent and independent prostate cancer and breast cancer and lung cancer.

7. A pharmaceutical composition for treatment of cancer in an animal, comprising a therapeutically effective amount of the compound of a compound having the following chemical structure:

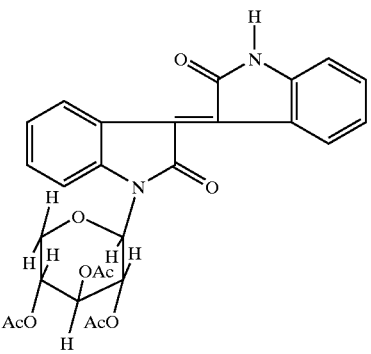

and a pharmaceutically acceptable carrier.

8. The pharmaceutical composition of claim 7, comprising an additional agent selected from the group consisting of radiotherapeutic agents, hormonal therapy agents, immunotherapeutic agents, chemotherapeutic agents, cryotherapeutic agents and gene therapy agents.

9. The pharmaceutical composition of claim 7, wherein the compound is formulated for oral administration.

* * * * *

UNITED STATES PATENT AND TRADEMARK OFFICE
CERTIFICATE OF CORRECTION

PATENT NO.    : 6,566,341 B1  Page 1 of 1
DATED         : May 20, 2003
INVENTOR(S)   : Wang et al.

It is certified that error appears in the above-identified patent and that said Letters Patent is hereby corrected as shown below:

Title page,
Item [56], References Cited, OTHER PUBLICATIONS:
Druker, B.J. et al., change "*BRC-ABL*" to -- *BCR-ABL* --; and delete the second occurrence of "Engl J"; and
Damiens, E., et al., change "*indirubin-3"-monoxime*" to -- *indirubin-3'-monoxime* --.
Item [57], ABSTRACT,
Line 3, delete "preventing or";
Lines 4-5, delete "and other related Isoindigo, Indigo and Indirubin derivatives are" and insert -- is --;
Line 8, delete "at least one of these derivatives" and insert -- NATURA --; and
Line 10, change "compounds" to -- compound --.

Column 10,
Line 65, change "Triacetyl-xylopransyl" to -- Triacetyl-xylopyranosyl --.

Column 18,
Line 15, delete "of the compound".

Signed and Sealed this

Second Day of September, 2003

JAMES E. ROGAN
*Director of the United States Patent and Trademark Office*